(12) United States Patent  
Olson

(10) Patent No.: US 6,632,371 B2
(45) Date of Patent: Oct. 14, 2003

(54) METHOD FOR CONTROLLING THE PROPORTION OF FLUID PASSING THROUGH A FILTER

(75) Inventor: Jeffrey A. Olson, Libertyville, IL (US)

(73) Assignee: Abbott Laboratories, Abbott Park, IL (US)

(*) Notice: Subject to any disclaimer, the term of this patent is extended or adjusted under 35 U.S.C. 154(b) by 0 days.

(21) Appl. No.: 09/923,560

(22) Filed: Aug. 7, 2001

(65) Prior Publication Data

US 2003/0034303 A1 Feb. 20, 2003

(51) Int. Cl.⁷ ............................................... B01D 37/00
(52) U.S. Cl. ..................... 210/808; 210/637; 210/650; 210/767; 422/101; 436/177; 436/178
(58) Field of Search ..................... 436/63, 177, 178, 436/180; 422/58, 101, 102; 210/637, 649, 650, 651, 767, 808, 436, 472, 416.1, 406

(56) References Cited

U.S. PATENT DOCUMENTS

| 4,948,564 A |   | 8/1990 | Root et al. ................... 422/101 |
| 5,124,041 A | * | 6/1992 | Sheer et al. ................. 436/178 |
| 5,240,861 A | * | 8/1993 | Bieri ........................... 436/178 |
| 6,054,100 A | * | 4/2000 | Stanchfield et al. ........ 422/102 |

FOREIGN PATENT DOCUMENTS

| EP | 0 718 618 A2 | 6/1996 |
| WO | 98/26859 | 6/1998 |

OTHER PUBLICATIONS

Copy of The PCT Search Report for Application PCT/US02/21817, Sep. 18, 2002.
Millipore Corporation, Passivation of Amicon® Microcon® Microconcentrators for Improved Recovery, Copyright 1999.
Millipore Corporation, Ultrafeet® PF–60 Concentrator Device, Copyright 1999.
Millipore Corporation, Microcon® Centrifugal Filter Devices, Copyright 1998.
Millipore Corporation, Microcon® Centrifugal Filter Devices User Guide, Copyright 1997.

* cited by examiner

Primary Examiner—Joseph Drodge
(74) Attorney, Agent, or Firm—David L. Weinstein

(57) ABSTRACT

An apparatus and a method for dividing a fluid into desired proportions by means of a filtering device. The method comprises the steps of:

(a) providing a filtration device, the filtration device comprising a filter; (b) adding a fluid to the filtration device, the fluid containing material dissolved or suspended therein; (c) placing the filtration device to which fluid has been added in a pressure vessel, the pressure vessel capable of withstanding a specified level of pressure relative to ambient pressure; (d) sealing the filtration device to form a trapped volume downstream of the filter; (e) increasing the pressure in the pressure vessel upstream of the filter; (f) allowing a period of time to elapse to allow the pressure downstream of the filter in the trapped volume to be substantially equal to the pressure upstream of the filter; (g) unsealing the filtration device; and (h) venting the pressure vessel.

6 Claims, 7 Drawing Sheets

METHOD FOR CONTROLLING THE PROPORTION OF FLUID PASSING THROUGH A FILTER

BACKGROUND OF THE INVENTION

1. Field of the Invention

This invention relates to filtration of a fluid by means of a filtration device; more particularly, the invention relates to a method and an apparatus for controlling the proportion of a fluid that passes through a filter in a filtration device.

2. Discussion of the Art

All processes for filtering fluids involve three components—the fluid itself, a filter, such as, for example, a membrane having a specified porosity, and means to force the fluid through the filter, such as, for example, a pump, gravity, centrifugal force. In some cases, the entire volume of fluid to be filtered is forced through the filter; in these cases, the desired product may be the fluid that has been forced through the filter. In other cases, the purpose of the filtering process is to concentrate a substance present in the fluid; in these cases, the desired product may be the portion of the fluid that has not been forced through the filter. In the latter cases, it may be desirable to control the volume of fluid retained in order to recover a product having a specific concentration of the substance. For example, it may be desired to concentrate, such as, for example, by a factor of 10 to 1, a specific protein dissolved or suspended in a small volume of an aqueous solution.

The conventional method for performing a concentrating operation involves depositing a sample of a fluid in a filter cartridge, such as, for example, a Microcon® centrifugal filter device, commercially available from Millipore Corporation. The loaded filter cartridge is then placed in a laboratory centrifuge and rotated at a high number of revolutions per minute. The orientation of the filter cartridge in the centrifuge would be such that the "g" forces created by the centrifugation operation would tend to drive the fluid through the filter and into a collection container, which is positioned downstream of the filter. The concentration factor is assumed to be a function of the duration of the centrifugation operation; the time required to achieve the desired concentration factor would be estimated by a trained operator. If the desired concentration factor is 10 to 1, then the desired volume retained upstream of the filter of the filter cartridge would be 1/10 of the volume initially loaded into the filter cartridge. At the end of the estimated time, the operator would stop the centrifuge and measure the proportion of fluid remaining upstream of the filter of the filter cartridge. If the proportion of fluid remaining upstream of the filter is determined to be approximately correct, the process would be complete. In most cases, however, it would be found that the volume of fluid retained upstream of the filter of the filter cartridge exceeded or fell short of the correct amount. If the volume retained upstream of the filter were too little, correction would be impractical because the concentration of the protein in the protein-containing solution would have been too high. If the volume retained upstream of the filter were too high, another cycle of centrifugation would be performed, with the duration again estimated by the operator in order to provide the desired concentration factor. This method, while effective, is laborious and inexact. If the number of samples to be concentrated at any one time is high, such as, for example, several dozen, the method quickly becomes impractical in a laboratory setting.

Accordingly, it would be desirable to develop a method for separating a solution or suspension into predetermined proportions by a means other than centrifugation, so that the separation can be controlled more accurately. In addition, it would be desirable to develop an automated method for separating a solution or suspension into predetermined proportions so that the proportioning process, once begun, can be performed without the need for an operator. It is further desired to develop a method such that a great number of proportioning processes can be performed simultaneously.

SUMMARY OF THE INVENTION

This invention provides an apparatus and a method for dividing a fluid into desired proportions by means of a filtering device. In one aspect, this invention provides a method for dividing a fluid into desired portions, the method comprising the steps of:

(a) providing at least one filtration device, the filtration device comprising a filter;

(b) adding the fluid to the at least one filtration device, the fluid containing material dissolved or suspended therein;

(c) placing the at least one filtration device to which fluid has been added in a pressure vessel, the pressure vessel capable of withstanding a specified level of pressure relative to ambient pressure;

(d) forming a trapped volume downstream of the filter;

(e) increasing the pressure in the pressure vessel upstream of the filter;

(f) allowing a period of time to elapse, the period of time being sufficient to allow the pressure downstream of the filter in the trapped volume to be substantially equal to the pressure upstream of the filter;

(g) unsealing the filtration device; and (h) venting the pressure vessel.

Optionally, the pressure within the pressure vessel can be reduced before the step (d), the step of forming the trapped volume. The filtration device preferably contains a membrane or barrier having a specified porosity, supported in a housing or in an equivalent element that can be mounted within the pressure vessel.

Many different types of fluids can be filtered by the method of this invention. One type of fluid that is particularly amenable to the method of this invention is a solution containing proteinaceous material dissolved therein. In this type of fluid, the solvent is typically an aqueous solvent.

The operating conditions of this method can be varied widely. For example, the pressure in step (e) can be raised to any pressure that can be withstood by the equipment. Pressures of as high as 215 psia are common in the method of this invention. The pressure in the optional step preceding step (d) can be reduced to as low a level as 0 psia. The pressure can be controlled to allow the division of the fluid into proportions ranging from about 100 to 1 to about 1 to 100. The size of the trapped volume can be varied by various techniques, such as, for example, insertion of plugs or inserts into the volume downstream of the filtration device or removal of plugs or inserts from the volume downstream of the filtration device.

In another aspect, this invention provides an apparatus for dividing a fluid into portions, the apparatus comprising:

(a) a pressure vessel, the pressure vessel capable of withstanding a specified level of pressure relative to ambient pressure;

(b) means for supporting at least one filtration device having a filter;

(c) means for sealing the at least one filtration device, whereby a trapped volume can be created downstream of the filter of the at least one filtration device inserted into the pressure vessel;

(c) means for creating negative pressure or positive pressure or negative and positive pressure relative to ambient pressure within the pressure vessel; and (d) means for venting the pressure vessel.

Means for sealing (b) include, but are not limited to, rings, gaskets, and similar types of seals. Means for providing negative pressure (c) include, but are not limited to, vacuum pumps. Means for providing positive pressure (c) include, but are not limited to, compressors, pressurized air lines, nitrogen cylinders. Means for providing positive or negative pressure within the pressure vessel further include, but are not limited to, solenoid valves, pneumatic valves, and the like.

The apparatus and method of this invention provide numerous benefits in the field of separating fluids into proportions. These benefits include the following:

(a) providing greater accuracy and repeatability of proportioning operations;

(b) simplifying control of the proportioning operation, i.e., filters may be allowed to remain in the apparatus for an indefinite period of time without any detrimental effect;

(c) providing the capability of performing proportioning operations on a great number of samples simultaneously;

(d) increasing the rapidity of the proportioning operation relative to a centrifugation operation, on account of a lower number of iterations;

(e) enabling complete automation of the proportioning operation after the operation has begun;

(f) providing the capability of varying proportions merely by adjusting the level of vacuum and the level of pressure in the pressure vessel; and (g) simplifying the introduction of samples into the apparatus and the removal of samples from the apparatus.

DETAILED DESCRIPTION

As used herein, the expression "filtration device" means a device that comprises a filter. The term "filter" means a porous substance through which a liquid is passed in order to remove constituents such as dissolved matter or suspended matter. An example of a filter suitable for use in this invention is a porous membrane, typically made of polymeric material. A filter can be used to separate dissolved matter from a liquid if the size of the pores in the filter is sufficiently small to prevent passage of the solute. For example, if a protein is dissolved in an aqueous solvent, a filter can be used to separate the protein from the solvent if the size of the pores in the filter is smaller than the size of the protein. The term "fluid" means any liquid. The expression "trapped volume" refers to a sealed region into which the fluid flows during the proportioning operation and in which fluid that has flowed is allowed to remain after the proportioning operation is completed.

The apparatus of this invention comprises:

(a) a pressure vessel, the pressure vessel capable of withstanding a specified level of pressure relative to ambient pressure;

(b) means for supporting at least one filtration device having a filter;

(c) means for sealing the at least one filtration device, whereby a trapped volume can be created downstream of the filter of the at least one filtration device inserted into the pressure vessel;

(c) means for creating negative pressure or positive pressure or negative and positive pressure relative to ambient pressure within the pressure vessel; and (d) means for venting the pressure vessel.

Figure 1:
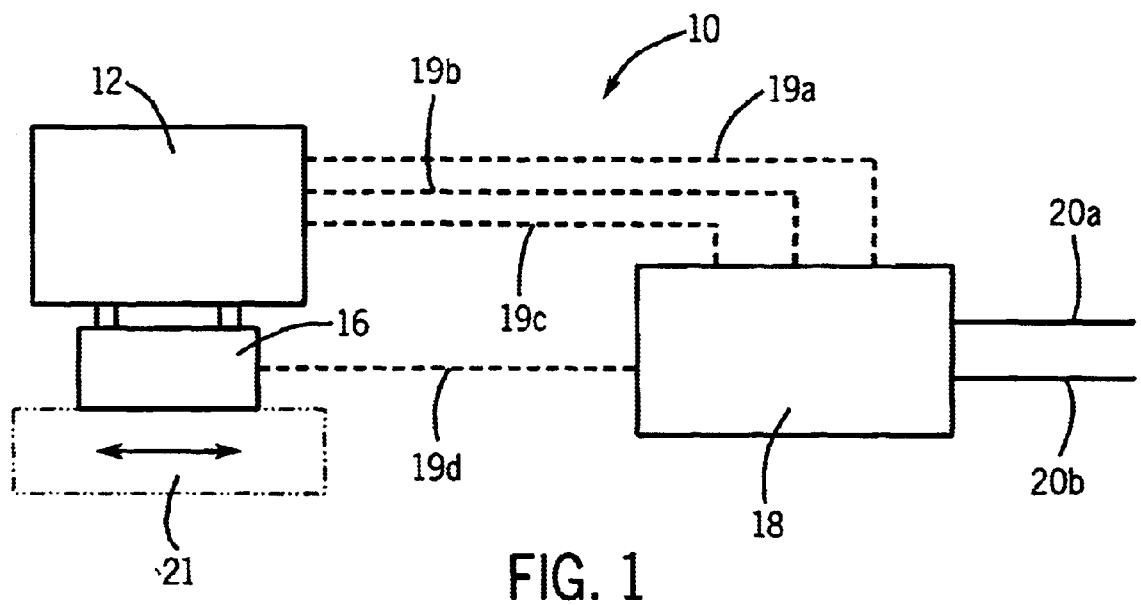
FIG. 1 is a schematic diagram illustrating a system for performing the method of this invention.

Referring now to FIG. 1, the apparatus 10 comprises a pressure vessel 12, which is capable of containing at least one filtration device 14, an actuator 16, a control unit 18, at least one pneumatic line that connects the control unit 18 to the pressure vessel 12, and at least one pneumatic line that connects the control unit 18 to the actuator 16. The pneumatic line 19a is a line for venting the pressure vessel 12 to the environment surrounding the pressure vessel 12. The pneumatic line 19b is a line for connecting a vacuum to the pressure vessel 12 to reduce the pressure in the pressure vessel 12. The pneumatic line 19c is a line for introducing compressed air or another gas into the pressure vessel 12 to increase the pressure in the pressure vessel 12. The pneumatic line 19d is a line for providing compressed air or another gas to cause the actuator 16 to operate. A pneumatic line 20a also connects the control unit 18 to a source of vacuum (not shown), and a pneumatic line 20b also connects the control unit 18 to a source of pressure (not shown). The control unit 18 typically comprises valves for regulating the flow of air or gas through the pneumatic lines 19a, 19b, 19c, 19d, 20a, and 20b. The control unit 18 also typically comprises a computer to control the operation of the aforementioned valves. It is also preferred that the assembly comprising the pressure vessel 12 and the actuator 16 be mounted on an agitator 21. The function of the agitator 21 is to accelerate the rate of the flow of fluid through the filter of the filtration device 14.

Figure 3A:
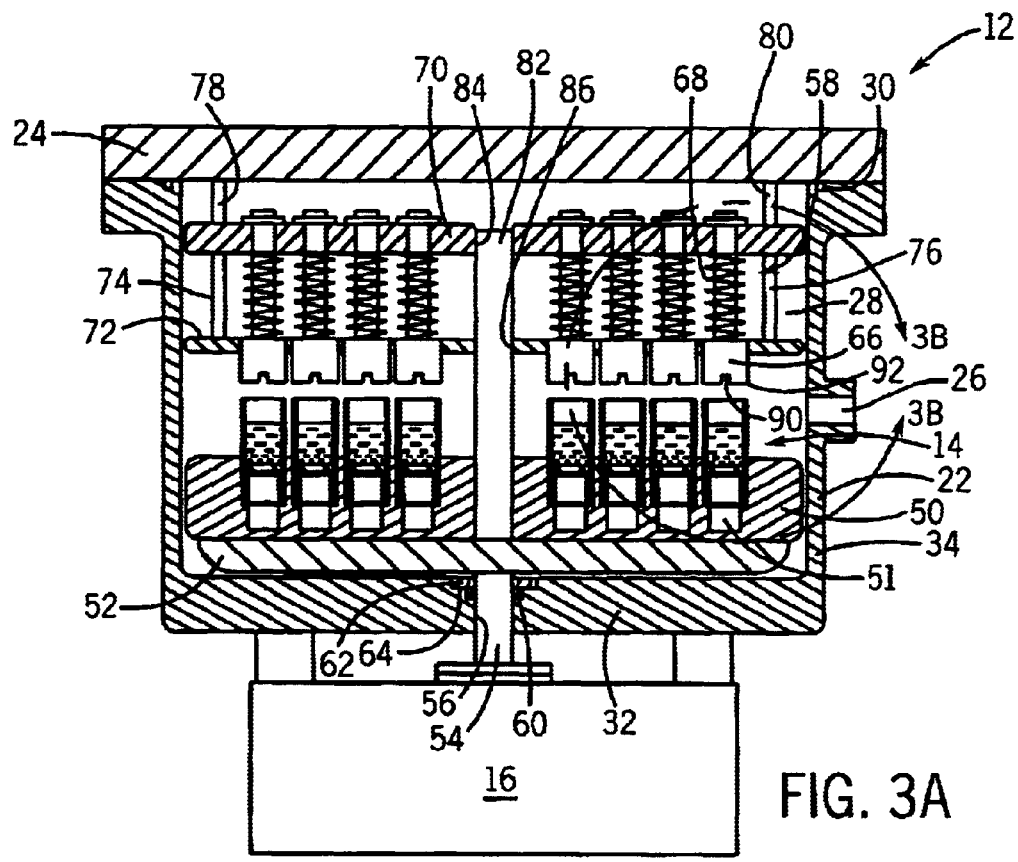
FIG. 3A is a side elevational view of a cross-section of the apparatus of this invention. The view shows the configuration inside the pressure vessel when the filtration devices are in an unclamped state.
Figure 4A:
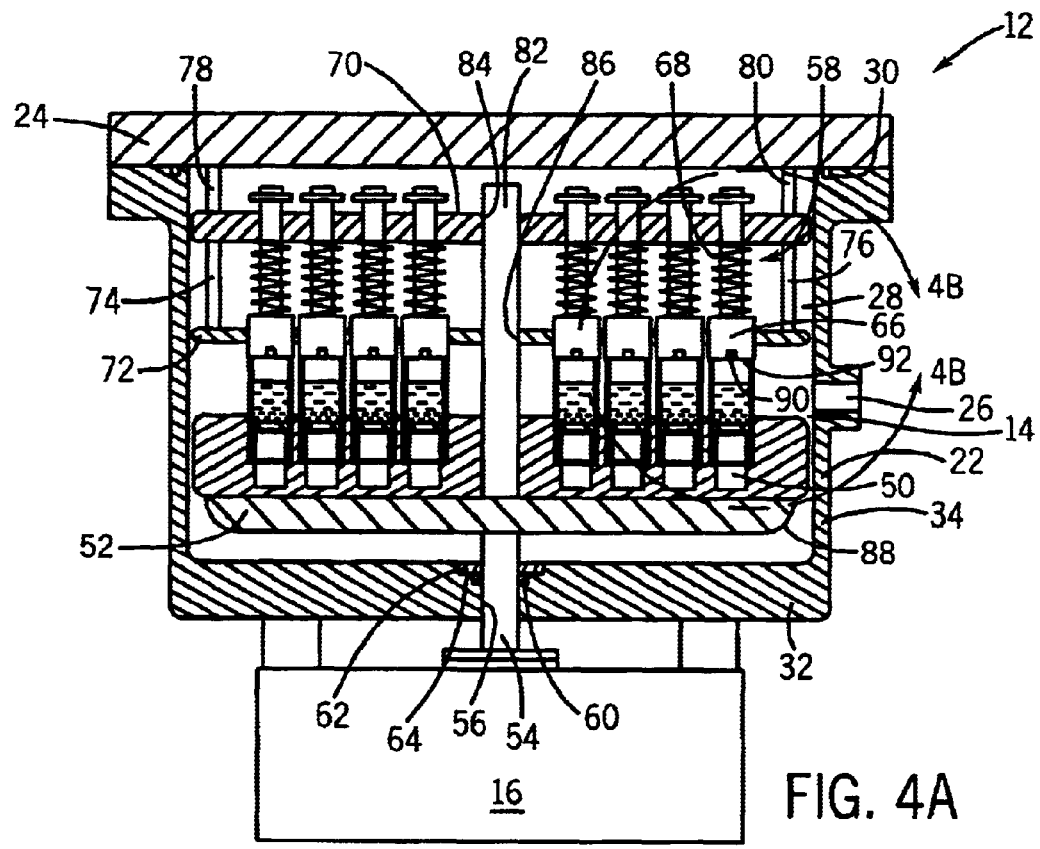
FIG. 4A is a side elevational view of a cross-section of the apparatus of this invention. The view shows the configuration inside the pressure vessel when the filtration devices are in a clamped state.

Referring now to FIGS. 3A and 4A, the pressure vessel 12 comprises a chamber 22 and a cover 24. The pressure vessel 12 must be designed to withstand the pressure and vacuum expected to be encountered during the operation of the method of this invention. The pressure and vacuum expected to be encountered during the operation of the method of this invention determine (1) the thickness of the walls of the chamber 22 and the cover 24 and (2) the materials of construction of the chamber 22 and the cover 24. The thickness of the walls and the materials of construction can be readily determined by one of ordinary skill in the art. As shown in FIGS. 3A and 4A, the chamber 22 of the pressure vessel 12 is in the shape of a cylinder, and the cover 24 of the pressure vessel 12 is in the shape of a cylinder. However, other shapes of these components are also suitable. For example, the pressure vessel 12 can be spherical in shape, with the chamber 22 being hemispherical and the cover 24 being hemispherical. The cover 24 can be secured to the chamber 22 by any means suitable for such a securing operation, such as, for example, bolts, tie rods, breach locking, and the like.

A passageway 26 formed in the chamber 22 of the pressure vessel 12 allows the passage of a gas, e.g., compressed air, nitrogen, into the pressure vessel 12 and out of the pressure vessel 12. The pressure within the air space 28 of the pressure vessel 12 can be varied by allowing a gas, preferably compressed air, to enter and leave the air space 28. A seal 30, e.g., an o-ring, is provided between the chamber 22 and the cover 24 to ensure the maintenance of the proper level of pressure or vacuum in the pressure vessel 12. The specifications of the seal 30 can be determined by one of ordinary skill in the art. In the embodiment shown in FIGS. 3A and 4A, the chamber 22 has a bottom wall 32 and a side wall 34.

Figure 2:
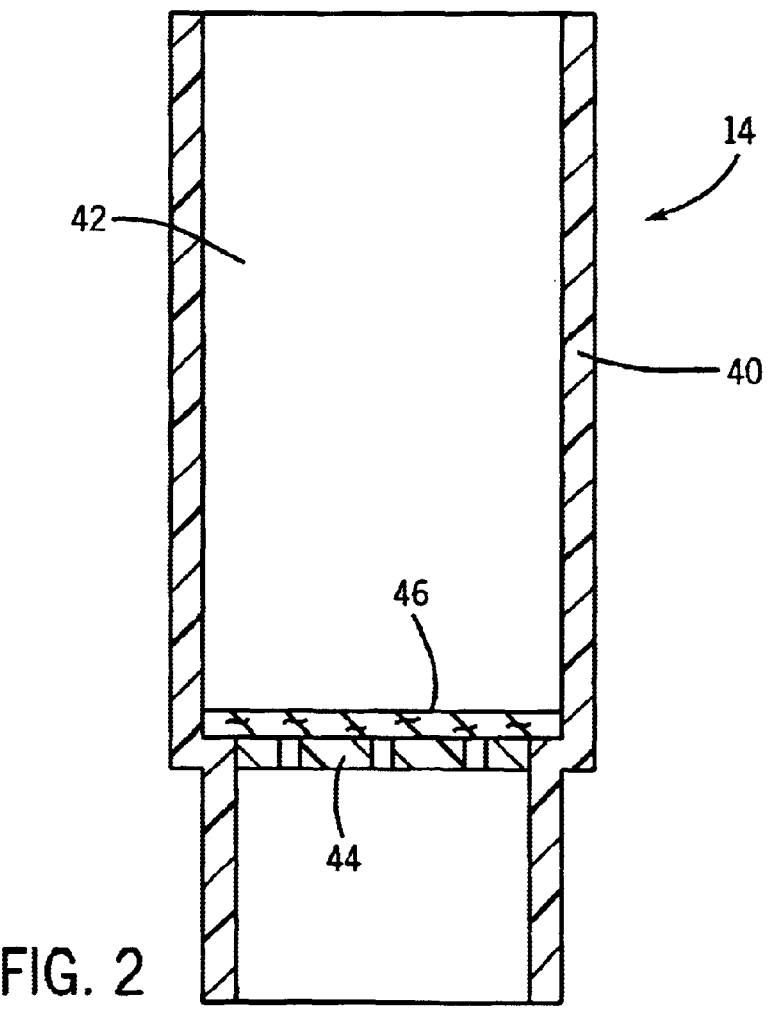
FIG. 2 is a side elevational view of a cross-section of a cartridge type filter device suitable for use in the method and apparatus of this invention.

Referring now to FIG. 2, the filtration device 14 comprises a housing 40, preferably having walls made from a plastic material. The housing 40 is preferably cylindrical in shape. The upper portion of the housing comprises a chamber 42 for receiving the fluid that is to undergo the proportioning operation. Immediately below the chamber 42 is a support 44 for supporting a filter 46, through which the fluid passes during the fluid proportioning process. Filtration devices 14 are well known to those of ordinary skill in the art. A representative example of a filtration device 14 is Microcon® centrifugal filter device, commercially available from Millipore Corporation, Bedford, Mass.

Figure 5:
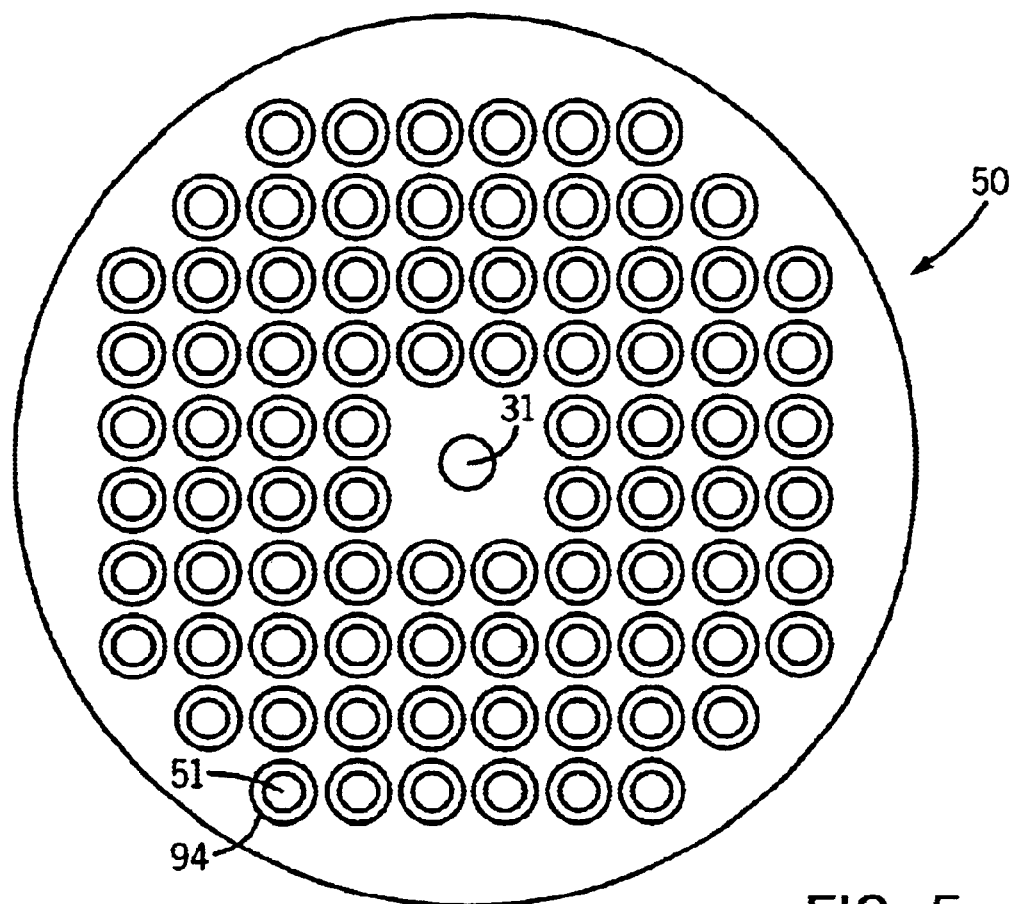
FIG. 5 is a plan view of a filtration device rack suitable for use in the method and apparatus of this invention.
Figure 6:
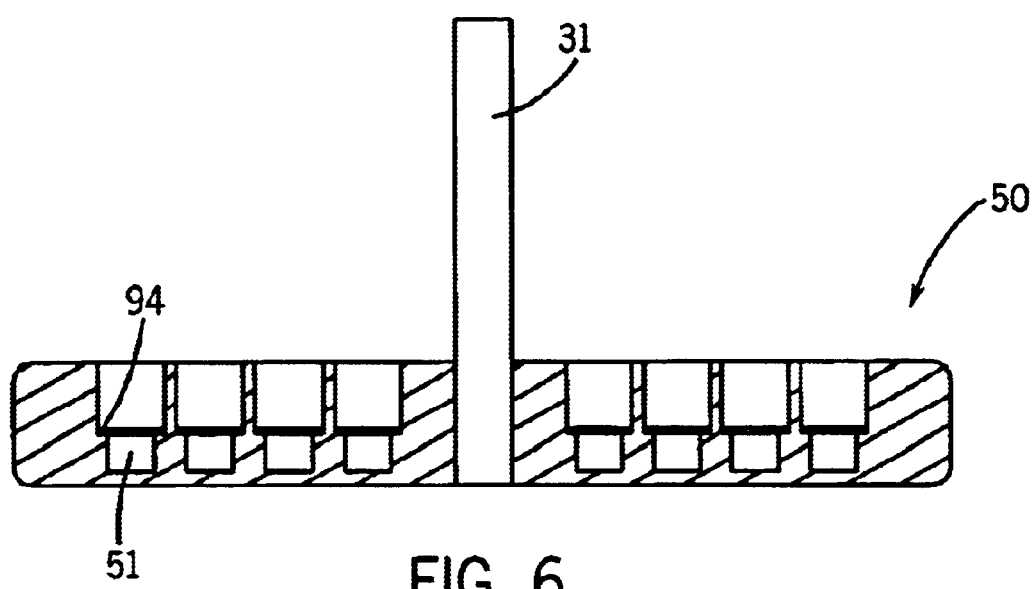
FIG. 6 is a side elevational view of a cross section of the filtration device rack shown in FIG. 5.

A filtration device rack 50 can be placed near the bottom wall 32 of the chamber 22 of the pressure vessel 12. The filtration device rack 50 in the embodiment shown in FIG. 5 is capable of holding at least one filtration device 14 and as many as eighty (80) filtration devices. Filtration devices can be inserted into recesses 51 machined into the filtration rack 50. A representative example of a filtration device suitable for use in this invention is shown in FIG. 2. Eight identical filtration devices, one of which is designated by the reference numeral 14, are shown in the filtration device rack 50 in FIGS. 3A and 4A.

The filtration device rack 50 rests on a support 52, which in turn is attached to a connecting rod 54. The connecting rod 54 passes through an opening 56 in the bottom wall 32 of the chamber 22 of the pressure vessel 12. The connecting rod 54 is connected to the actuator 16. The purpose of the actuator 16 is to raise and lower the support 52 and the filtration device rack 50 a small distance from the bottom wall 32 of the pressure vessel 12. The actuator 16 raises or lowers the filtration device rack 50 relative to a filtration device clamp assembly 58 at appropriate times during the operation of the apparatus 10. The actuator 16 can be driven by compressed air, by hydraulic pressure, by a screw, by rack and pinion, or by any other means for this purpose known to one of ordinary skill in the art. Another seal 60, e.g., an o-ring, is used to seal the space between the connecting rod 54 and the opening 56 in the bottom wall 32 of the chamber 22 of the pressure vessel 12. The specifications of the seal 60 can be determined by one of ordinary skill in the art. A cover plate 62 traps the seal 60 in a recess 64 machined into the bottom wall 32 of the chamber 22 of the pressure vessel 12.

Figure 3B:
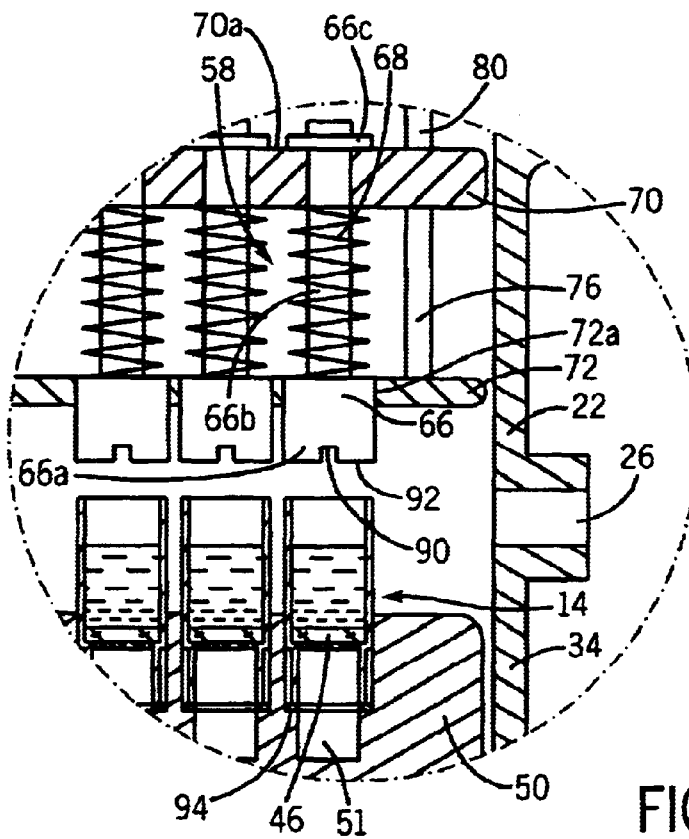
FIG. 3B is an enlarged view of the encircled portion of the view shown in FIG. 3A.

The filtration device clamp assembly 58 is positioned above the filtration device rack 50. Eight identical filtration device clamp assemblies, one of which is designated by the reference numeral 58, are shown in FIGS. 3A and 4A. The filtration device clamp assembly 58 comprises at least one filtration device clamp 66. Eight identical filtration device clamps, one of which is designated by the reference numeral 66, are shown in the embodiment depicted in FIGS. 3A and 4A. The filtration device clamp assembly 58 further comprises at least one means 68 for biasing a filtration device clamp towards the filtration device 14. The preferred biasing means is a spring. A representative example of a spring suitable for use in this invention is a stainless steel spring having part number LC-035D-13-SS, commercially available from Lee Spring Company. This spring provides a clamping force of approximately five (5) pounds. Eight identical springs, one of which is designated by the reference numeral 68, are shown in FIGS. 3A and 4A. The filtration device clamp assembly 58 further comprises an upper plate 70, a lower plate 72, and at least one spacer. Two spacers 74 and 76 are shown in FIGS. 3A and 4A. The filtration device clamps 66 are biased downward (toward the filtration device 14) by the springs 68 and guided (or directed) by openings 70a formed in the upper plate 70 that are in register with openings 72a formed in the lower plate 72 (see FIGS. 3B and 4B). Spacers 74 and 76 maintain the proper spacing between the upper plate 70 and the lower plate 72. A sufficient amount of clearance is provided above the filtration device clamps 66 so that the filtration device clamps 66 are capable of a small upward displacement relative to the upper plate 70 and the lower plate 72. In the embodiment shown in FIGS. 3A, 3B, 4A, and 4B, each filtration device clamp 66 comprises a head 66a and a shaft 66b (see FIGS. 3B and 4B). Each of the shafts 66b is capable of vertical movement in the openings 70a formed in the upper plate 70 and the openings 72a formed in the lower plate 72. Another set of spacers 78 and 80 provide proper spacing distance between the filtration device clamp assembly 66 and the cover 24. A guide post 82 attached to the center of the filtration device rack 50 is fitted through an opening 84 in the upper plate 70 and an opening 86 the lower plate 72. The guide post 82 constrains the motion of the filtration device rack 50, thereby preventing it from tilting during operation.

Figure 4B:
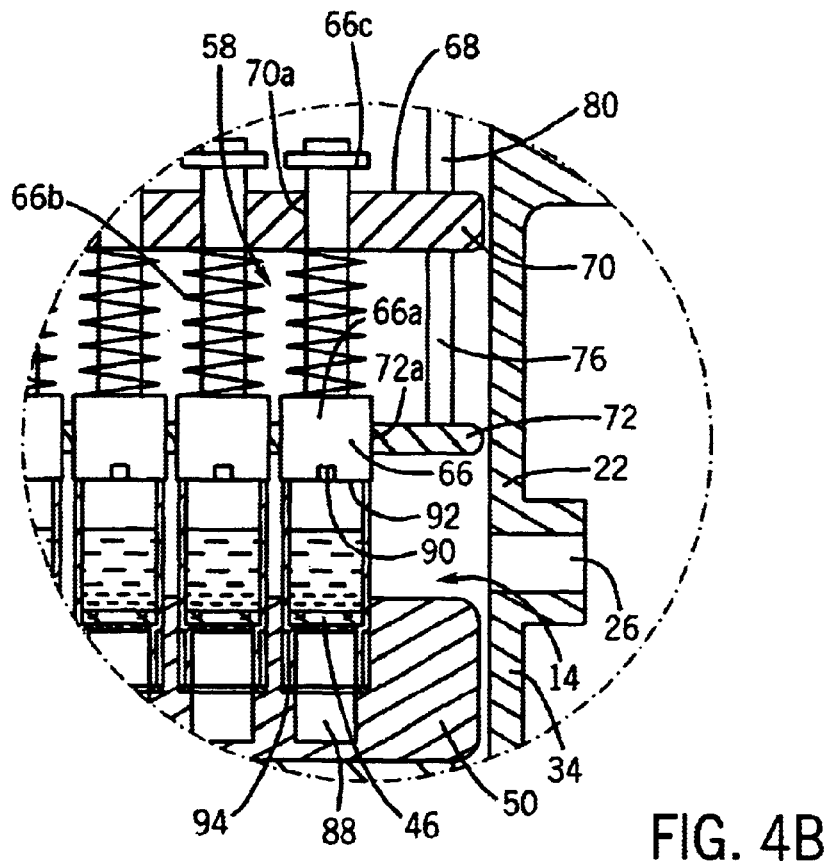
FIG. 4B is an enlarged view of the encircled portion of the view shown in FIG. 4A.

When the filtration device rack 50 is raised, the filtration devices 14 are said to be in a clamped state. In this position, as shown in FIGS. 4A and 4B, the filtration device clamps 66 push downward on the filtration devices 14 with forces determined by the springs 68. The purpose of this clamping action is to create a trapped volume 88 downstream of the filters in the filtration devices 14. That is, when the filtration device rack 50 is clamped, the trapped volume 88 is hermetically sealed from the air space 28 in the rest of the pressure vessel 12. In contrast, the air space 28 upstream of the filters in the filtration devices 14 is maintained at the same pressure as the air space 28 in the pressure vessel 12. Maintenance of this equalization of pressures can be accomplished by a channel 90, which is formed in the area 92 of each filtration device clamp 66 facing the filtration device. In order to maintain a hermetic seal, a seal 94, e.g., an elastomeric washer, is used to seal the space between the filtration device 14 and the filtration device rack 50. The specifications of the seal 94 can be determined by one of ordinary skill in the art. A representative example of a seal 94 suitable for use in this invention is made by Apple Rubber products. This seal 94 has an outside diameter of 0.375 inch and an inside diameter of 0.25 inch. The thickness of the seal 94 is 0.032 inch. The material of the seal is a silicone elastomer having a hardness of 40 durometer (Shore A scale).

When the filtration device rack 50 is not in the clamped state, the trapped volume 88 is not sealed from the air space 28 in the rest of the pressure vessel 12. In this state, the pressure level that exists in the trapped volume 88 will be the same as that in the rest of the air space 28. A collar 66c prevents the filtration device clamp 66 from falling out of the upper plate 70 and the lower plate 72 when the filtration device rack 50 is not in the clamped state.

Operation

The method of this invention comprises the following steps:

(a) providing at least one filtration device, the filtration device comprising a filter;

(b) adding the fluid to the at least one filtration device, the fluid containing material dissolved or suspended therein;

(c) placing the at least one filtration device to which fluid has been added in a pressure vessel, the pressure vessel capable of withstanding a specified level of pressure relative to ambient pressure;

(d) forming a trapped volume downstream of the filter;

(e) increasing the pressure in the pressure vessel upstream of the filter;

(f) allowing a period of time to elapse, the period of time being sufficient to allow the pressure downstream of the filter in the trapped volume to be substantially equal to the pressure upstream of the filter;

(g) unsealing the filtration device; and (h) venting the pressure vessel.

In an alternative embodiment, the optional step of reducing the pressure within the pressure vessel to a level below ambient can be included subsequent to step (c) and prior to step (d).

The operation of this invention involves a sequence of steps in which the level of pressure within the pressure vessel 12 varies as a function of the position of the filtration device rack 50. In other words, the level of pressure within the pressure vessel 12 depends on whether or not the filtration device rack 50 is in the clamped state. The timing of the steps in this sequence, as well as the level of pressure, is controlled by the control unit 18. See FIGS. 7A, 7B, 7C, 7D, 7E, and 7F.

In order to simplify the explanation of the operation of the method and apparatus of this invention, the following set of conditions is selected:

| | |
|---|---|
| Initial volume of fluid to be proportioned = | 400 μL |
| Volume of fluid to be retained upstream of the filter = | 30 μL |
| Pressure level = | 115 psia |
| Vacuum level = | 2 psia |
| Size of trapped volume = | 376 μL |

The filtration device is a Microcon® centrifugal filter device (Millipore Corporation, 500 μL capacity on the upstream side of the filter). The values of the conditions selected herein are arbitrary; other levels of pressure and vacuum can be used, if so desired. Because the volume of fluid to be retained upstream of the filter is 30 μL, it is desired to force 370 μL of the initial volume of fluid through the filtration device and then prevent additional flow of fluid thereafter. The following calculations further demonstrate the operating principle of the method and apparatus:

Vacuum=2 psia

Desired flow through volume ($V_{ft}$)=400 μL−30 μL=370 μL $P_f$=final pressure in trapped volume at equilibrium=115 psia $P_i$=initial pressure in trapped volume after vacuum has been applied=2 psia $V_i$=initial volume of air in trapped volume $V_f$=final volume of air in trapped volume $V_r$=volume of fluid retained upstream of the filter in the filtration device Assuming isothermal compression of the air trapped in the trapped volume $$P_f/P_i = V_i/V_f \quad (1)$$

$$P_f/P_i = V_i/(V_i - V_{ft}) \quad (2)$$

115 psia/2 psia=$V_i/(V_i$−370 μL)

$V_i$=376.5 μL

Therefore, the desired volume for the trapped volume is 376.5 μL.

Figure 7A:
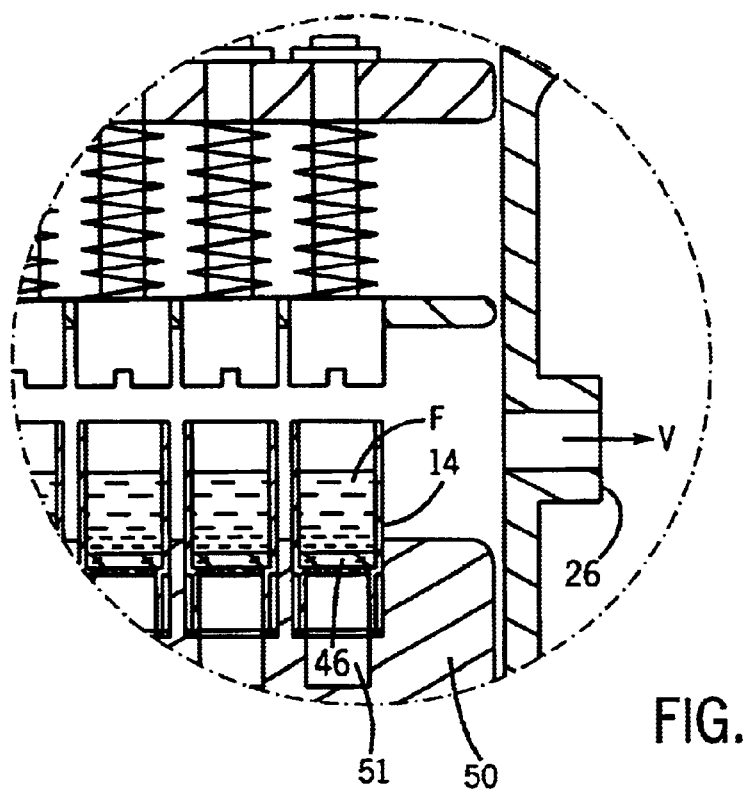
FIGS. 7A, 7B, 7C, 7D, 7E, and 7F are diagrams illustrating the steps employed in the method of this invention.

The method and apparatus of this invention can accomplish this proportioning of a sample of fluid by means of the sequence of steps depicted in FIGS. 7A, 7B, 7C, 7D, 7E, and 7F. In this series of figures, for the sake of simplification, only three each of the filtration device 14 and filtration device clamp assembly 58 are shown. Referring now to FIG. 7A, each filtration device 14 is filled with liquid (400 μL), designated by the letter "F", and placed on top of the seal 94 in the filtration device rack 50. The cover 24 of the pressure vessel 12 is closed and secured, preferably by means of bolts, so that the pressure vessel 12 is sealed to the environment that is outside of the pressure vessel 12. The filtration device rack 50 is set in the unclamped state so that no clamping force is exerted on the filtration device 14. A vacuum is connected to the inlet 26 of the pressure vessel 12 so that the entire interior volume of the pressure vessel 12, including the volume thereof downstream of the filter 46, is reduced to a level of pressure of 2 psia. The pneumatic line used for reducing the level of pressure is the pneumatic line 19b. During this step no fluid is forced through the filter of the filtration device 14 because no pressure differential exists across the filter. An arrow and the letter "V" indicates that a vacuum is being applied.

Figure 7B:
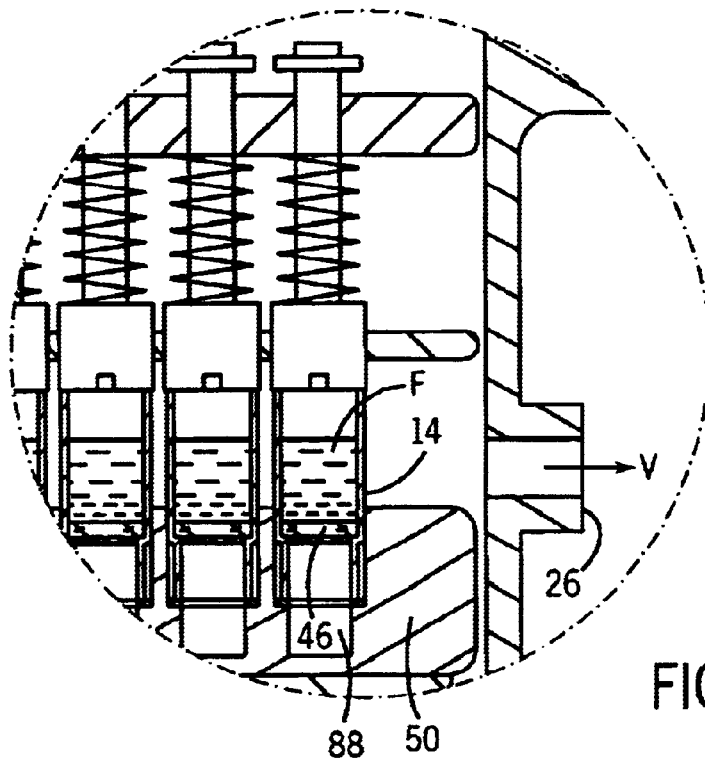

Referring now to FIG. 7B, while the vacuum is still being applied, the filtration device rack 50 is moved a sufficient distance by means of the actuator 16 to set the filtration device rack 50 into the clamped state, wherein a downward force is exerted on the filtration device 14. The pneumatic line used for supplying compressed air or gas for moving the actuator 16 is the pneumatic line 19d. This downward force compresses the seal 94 between the filtration device 14 and the filtration device rack 50, thereby sealing the trapped volume 88 from the rest of the environment inside the pressure vessel 12. At this point, the pressure within the pressure vessel 12, as well as within the trapped volume 88, remains at a level of 2 psia. An arrow and the letter "D" indicates that a downward force is being applied.

Figure 7C:
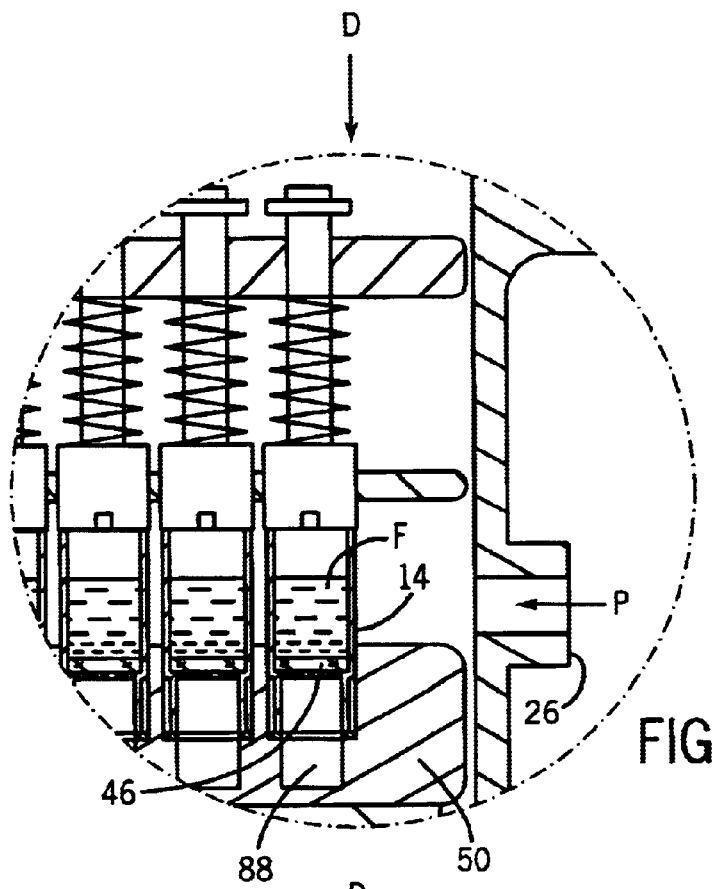

Referring to FIG. 7C, the inlet 26 to the pressure vessel 12 is switched away from the vacuum and connected to a source of compressed air. After a sufficient period of time has elapsed, the absolute pressure in the chamber rises to 115 psia, but the pressure in the trapped volume 88 continues to be 2 psia, thereby resulting in a pressure difference of 113 psia across the filter 46. The pneumatic line used for supplying compressed air to raise the pressure in the pressure vessel 12 is the pneumatic line 19c. This pressure difference exerts a net force on the fluid and the fluid begins to flow through the filter 46 into the trapped volume 88. An arrow and the letter "P" designates an increase in pressure brought about by the introduction of compressed air into the pressure vessel 12.

Figure 7D:
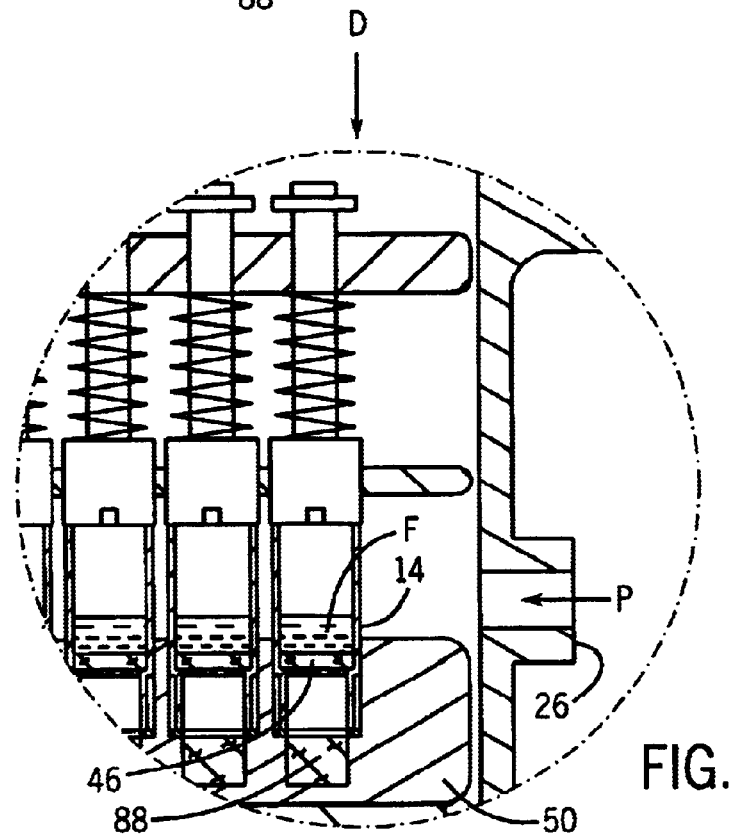

Referring to FIG. 7D, after an initial period of time has elapsed, e.g., 15 minutes, a portion of the fluid has flowed through the filter 46 and into the trapped volume 88. Because the trapped volume 88 is sealed, and the fluid occupies a portion of this trapped volume 88, the trapped air, which was at a pressure of 2 psia at the beginning, is compressed, thereby resulting in a higher pressure in the trapped volume 88, e.g., about 30 psia. It should be noted that a pressure difference still exists across the filter 46, which pressure difference continues to drive fluid through the filter 46 into the trapped volume 88.

Figure 7E:
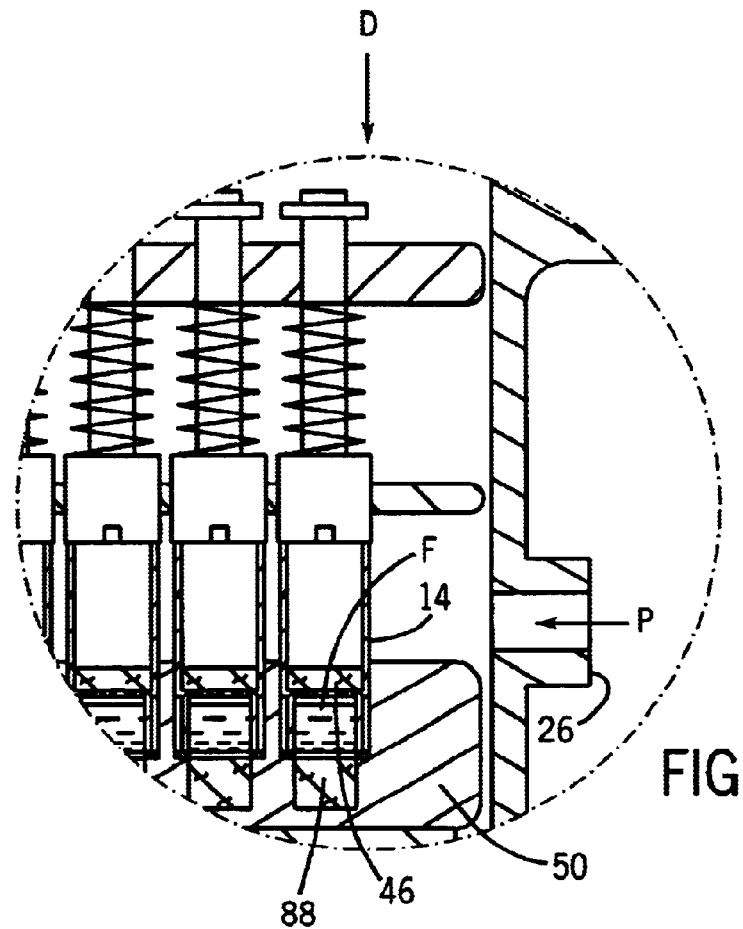

Referring to FIG. 7E, after a subsequent period of time has elapsed, a condition of equilibrium is reached. By this time, most of the fluid has flowed through the filter 46 and the pressure in the trapped volume 88 is now 115 psia, the same pressure as that within the air space 28 of the pressure vessel 12. Because the net pressure across the filter 46 is now zero, all flow of fluid stops. The size of the trapped volume 88 determines the volume of fluid that will be retained upstream of the filter at the completion of the process. If the size of the trapped volume 88 has been specified carefully, the volume of fluid retained upstream of the filter will be near the desired amount—in this case 30 $\mu$L. The duration of the filtration process is not critical; after the system has attained the state of equilibrium, the filtration device 14 can be held in the pressure vessel 12 indefinitely and no further flow of fluid will take place. The end point of the filtration process is determined solely by the size of the trapped volume 88 and the levels of pressure and vacuum used in the process.

Figure 7F:
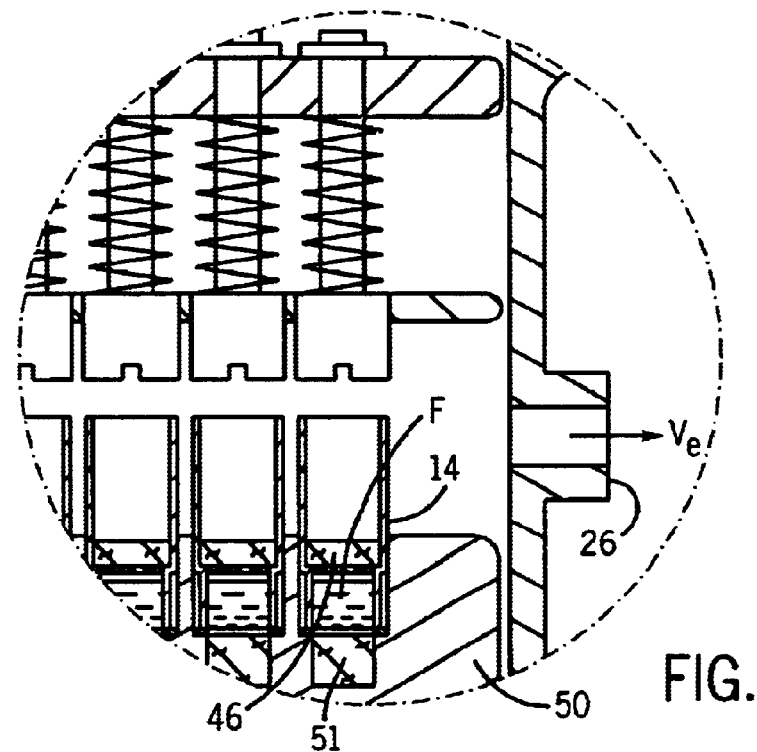

Referring now to FIG. 7F, in the final step, the filtration device rack 50 is moved to the unclamped state, and the gas (air) within the pressure vessel 12 is vented to the atmosphere. The pneumatic line used for venting the gas to the atmosphere is the pneumatic line 19a. When the clamping pressure against the seal 94 is removed, the air trapped downstream of the filter is now free to escape harmlessly. If the pressure vessel 12 were vented without unclamping the filtration device 14, the filter 46 would rupture, due to the force of the trapped air downstream of the filter. If the filter were to rupture, the fluid retained upstream of the filter would be free to mix with the fluid collected downstream of the filter, thereby defeating the purpose of the method. An arrow and the abbreviation "Ve" designates the flow of air or gas in the venting step.

It should be noted that the method and the apparatus of this invention employ the principle that fluid flow must cease when there is no pressure differential across the filter. By carefully specifying the levels of pressure and vacuum and the size of the trapped volume 88, the point at which there is no pressure difference across the filter, and thus no more flow of fluid, can be selected. In this way, any desired fraction of the fluid can be retained upstream of the filter.

The apparatus also provides means for making modest adjustments to the proportion of fluid retained upstream of the filter by varying the clamping force. Because the seal 94 is somewhat compressible, an increase to the clamping force increases the compression of the seal 94 and reduces the size of the trapped volume 88. This increase in clamping force can be brought about by, for example, using a stronger spring, which provides a higher compressive force. For a given level of pressure, a reduction in the size of the trapped volume 88 will lead to a decrease in the volume of fluid that can flow through the filter, $V_{ft}$ and, thus, an increase in the volume of fluid retained upstream of the filter, $V_r$. Conversely, for a given level of pressure, a decrease in the clamping force has the effect of increasing the size of the trapped volume 88. An increase in the size of the trapped volume will lead to an increase in the volume of fluid that can flow through the filter, $V_{ft}$, and, thus, a decrease in the volume of fluid retained upstream of the filter, $V_r$. Therefore, by careful manipulation of the clamping force, fine adjustments can be made to the system.

As stated previously, some of the major benefits attributable to the method and apparatus of this invention include the following:

(a) greater accuracy and repeatability of proportioning operations;

(b) simplified control of the proportioning operation;

(c) the capability of performing proportioning operations on a great number of samples simultaneously;

(d) increased rapidity of the proportioning operation relative to a centrifugation operation, on account of a lower number of iterations;

(e) complete automation of the proportioning operation after the operation has begun;

(f) the capability of varying proportions merely by adjusting the level of vacuum and the level of pressure in the pressure vessel; and (g) simplified introduction of samples into the apparatus and the removal of samples from the apparatus.

Various modifications and alterations of this invention will become apparent to those skilled in the art without departing from the scope and spirit of this invention, and it should be understood that this invention is not to be unduly limited to the illustrative embodiments set forth herein.

What is claimed is:

1. A method for dividing a fluid containing material dissolved or suspended therein into desired proportions, said method comprising the steps of:

(a) providing at least one filtration device, said filtration device comprising a filter;

(b) adding said fluid to said at least one filtration device;

(c) placing said at least one filtration device to which said fluid has been added in a pressure vessel, said pressure vessel capable of withstanding a specified level of pressure relative to ambient pressure;

(d) sealing said at least one filtration device to form a trapped volume downstream of said filter, said trapped volume being hermetically sealed from air space in remainder of said pressure vessel, whereby mass of air in said trapped volume is sealed against escape or entry of air;

(e) increasing the pressure in said pressure vessel upstream of said filter;

(f) allowing a period of time to elapse, said period of time being sufficient to allow said fluid to flow through said filter into said trapped volume, whereby the pressure downstream of said filter in said trapped volume is allowed to reach a level that is substantially equal to the pressure upstream of said filter, whereby a desired proportion of said fluid passes through said filter;

(f) unsealing said at least one filtration device; and (g) venting said pressure vessel.

2. The method of claim 1, wherein said filter is a porous membrane.

3. The method of claim 1, wherein said material suspended or dissolved in said fluid comprises a protein.

4. The method of claim 1, wherein said pressure in step (e) exceeds the initial pressure in said trapped volume.

5. The method of claim 4, wherein the size of said trapped volume and the level of pressure in step (e) and the initial pressure in said trapped volume determine the proportion of fluid that will be retained upstream of said filter.

6. The method of claim 1, wherein the pressure in said pressure vessel is reduced prior to step (d).

* * * * *